United States Patent [19]

Losada

[11] Patent Number: 4,653,512
[45] Date of Patent: Mar. 31, 1987

[54] BLOOD COLLECTION ASSEMBLY

[75] Inventor: Robert J. Losada, Astoria, N.Y.

[73] Assignee: Becton, Dickinson and Company, Franklin Lakes, N.J.

[21] Appl. No.: 743,250

[22] Filed: Jun. 11, 1985

[51] Int. Cl.[4] ............................................. A61B 5/14
[52] U.S. Cl. ...................................... 128/763; 128/767
[58] Field of Search ....................... 128/760, 762–768, 128/770–771

[56] References Cited

U.S. PATENT DOCUMENTS

| | | | |
|---|---|---|---|
| 4,024,857 | 5/1977 | Bletcher et al. | |
| 4,215,700 | 8/1980 | Crouther et al. | 128/763 |
| 4,250,893 | 2/1981 | White | 128/765 |
| 4,397,318 | 8/1983 | Burns | 128/763 |
| 4,411,163 | 10/1983 | White | 73/864.02 |

*Primary Examiner*—Kyle L. Howell
*Assistant Examiner*—Angela D. Sykes
*Attorney, Agent, or Firm*—Robert P. Grindle

[57] ABSTRACT

A cap is provided for a blood microcollection container which cap incorporates a partially open tubular and tapered scoop arrangement for engaging a puncture wound, and rapidly receiving blood from the wound. Longitudinally extending ribs serve to define and maintain a blood flow and an air venting passage in the collector, while preventing blood "hang-up" caused by capillary action in the blood flow passage of the collector. With this invention, the time of transfer is reduced substantially because less precise positioning is required of the scoop, and blood "hang-up" in the transfer passage is avoided.

14 Claims, 8 Drawing Figures

BLOOD COLLECTION ASSEMBLY

BACKGROUND AND STATEMENT OF THE INVENTION

This invention relates to a blood collection assembly incorporating a microcollection container. The invention is an improvement over the collection assembly described and claimed in U.S. Pat. No. 4,397,318, issued Aug. 9, 1983, which is hereby incorporated by reference in its entirety. Reference should be made to that patent for background information concerning the teachings of the invention here. The earlier patent involved the use of a scoop collector for connection to a blood microcollection container for engaging a puncture wound to obtain a blood sample from an individual for subsequent examination of that sample for the determination of the presence or absence of some disease or other problem in a patient. The scooptype blood collection device provides a substantially larger engaging surface for engaging the puncture for collecting the blood, and a substantially larger transfer surface for rapidly transferring the blood from the collector into the microcollection container. Because of the relatively large engaging surface for engaging the puncture wound, the arrangement does not require a precise positioning of the scoop engaging surface in order to initiate and rapidly transfer a quantity of blood to the microcollection container.

As will be appreciated by practitioners-in-the-art, recent advancements in analytical instrumentation have made it possible to carry out a variety of hematological or chemical diagnostic procedures on very small quantities of blood. Because of this, a patient's finger, earlobe, or infant's heel may be punctured and a very small quantity of blood rapidly collected into a microcollection container for such testing. Such arrangements obviate the need to withdraw venous blood from patients. However, such collection arrangements must be such that the blood is rapidly collected prior to any coagulation thereof. In the past, prior to the scoop collector disclosed in the above-noted U.S. Pat. No. 4,397,318, a cap or top arrangement was configured to fit on the top of a microcollection container with the top having an integral capillary tube for engaging the puncture and transferring blood to the container. However, with such an arrangement, the tip of the capillary tube had to be arranged precisely adjacent the puncture wound and the entire apparatus had to be so positioned that the blood flow along the bottom surface of the tubular microcollection container moved continuously in order to engage the surface of the container. Otherwise, if a precise positioning was not carried out, capillary action was not initiated or slowed with subsequent clotting. Representative such collectors are taught in U.S. Pat. No. 4,024,857, issued May 24, 1977.

One problem with the scoop collector taught and claimed in U.S. Pat. No. 4,397,318, although the arrangement taught therein is highly efficient for the rapid collection of a blood sample into a microcollection container, is the fact that because of the very rapid collection of blood by the scoop collector, the separate blood passage in the collector becomes somewhat occluded by the blood passing therethrough and there is "hang-up" on the walls thereof by capillary action. While this phenomenon is only momentary, it can delay blood collection in situations where the technician is, for example, attempting to take a blood sample, from a screaming, wiggly baby.

With this invention, by contrast, a scoop arrangement is incorporated into a blood microcollection assembly in such a way that the scoop collector does not have a separate vane or wall separating the air vent passage in the collector from the blood passage. It has, instead only longitudinally extending ribs extending only part way into the combined blood/air passage. The ribs contain blood flow so that the blood does not touch the walls of the combined passage through the entire circumferential extent thereof. For this reason, capillary action causing blood "hang-up" does not take place and blood flows rapidly through the passage. This in turn reduces blood sample waste in the very small total quantities involved, resulting in a larger specimen yield. Moreover, such an arrangement reduces the need for incorporating expensive wetting agents in the collector devices of the invention.

Other objects and advantages of this invention will be apparent from the following description, the accompanying drawings and the appended claims.

DETAILED DESCRIPTION OF THE INVENTION

Figure 1:
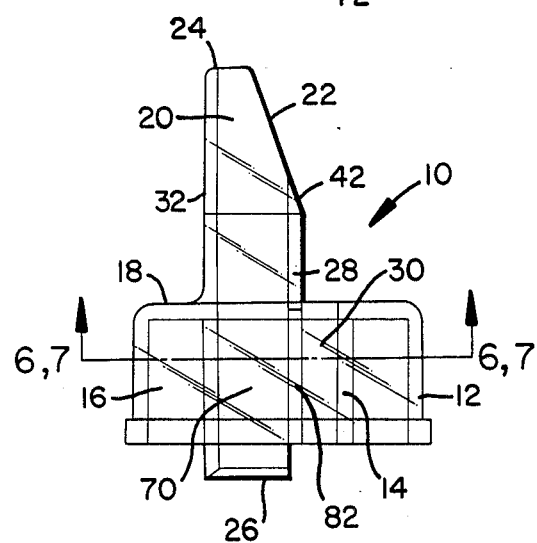
FIG. 1 is a side elevational view of the blood collector of the invention wherein the collector is illustrated as incorporated into a cap or top arrangement for a microcollection container.

Referring to the drawings in which like characters or reference refer to like parts throughout the several views thereof, FIG. 1 illustrates the invention as employed in a cap arrangement therein the collector of the invention is integrally formed with the cap. In this connection, it should be emphasized that the collector of the invention is comprised of a transparent or translucent resin material in order to facilitate viewing of the blood flow passage through the collector. For this reason, all of the views are of transparent parts.

In FIG. 1, the device 10 includes a cap or top for a microcollection container with concentric spaced apart annular skirts 12, 14 joined together by a top wall 18. The annular space 16 defined by the spaced skirts 12, 14 defines a space for receiving in press fit engagement the top edge of a microcollection tube. This arrangement defines an attaching means. As can be seen in FIG. 1, a tubular microcollection scoop 20 is incorporated into the cap arrangement and extends therethrough from an engaging end 24 to an inner end 26, with the latter for extending into and engaging the adjacent surface of a microcollection container, when the cap or top 10 is positioned on the top edge of the container.

Figure 2:
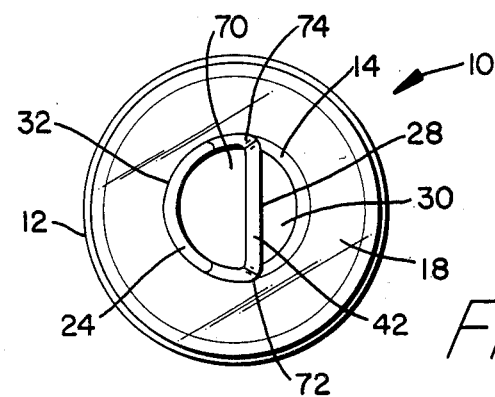
FIG. 2 is a top plan view of the collector of FIG. 1.

The upper portion of scoop 20 does not extend to the outer engaging end 24 of scoop 20, as shown in FIG. 1. The upper wall 28 of scoop 20 ends at 42 to define a tapered upper edge 22 extending from tip 24 to the end 42 of upper wall 28. Upper wall 28 serves as a vane or separator which partially defines a vent area 30 extending through cap 10. The vent provides for air displacement from the microcontainer when blood is introduced into the container through scoop 20. The semi-annular lower wall 32 of scoop 20, at the outer end or tip 24 extends through an angle as shown in FIG. 2 of about 120° for defining a substantially larger engaging surface for engaging a puncture wound than the angular extent of a capillary tube engaging the same puncture for initiating capillary action as discussed in detail in the above-noted U.S. Pat. No. 4,397,318.

The upper wall of vane 28 and the lower semicircular wall 32 define the relatively large blood transfer passage 70 for transferring, rapidly, a quantity of blood into the microcollection container. The inner end 26 of the passage 70 has a semi-tubular engaging angular surface defined by the side edges 72, 74 of vane 28, as shown in FIG. 2, with this end surface for engaging the internal surface of the microcollection container being about 220°, again as described in U.S. Pat. No. 4,397,318.

Figure 4:
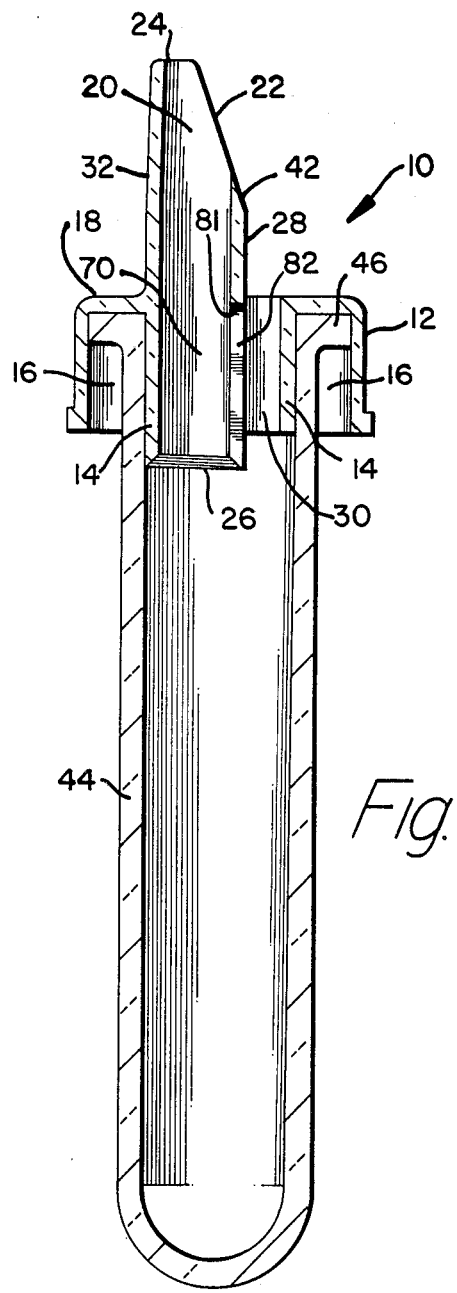
FIG. 4 is a side elevational view in section of a microcollection container having disposed on the top thereof an integral scoop collector and top illustrating the invention.

Referring now to FIG. 4, the cap or top 10 of the invention is shown press fit on the upper end 46 of a tubular microcollection container 44. As will be appreciated, other arrangements may be made for engagement and connection of top 10 with the top edge of a microcollection container 44. In addition, the microcollection container may be configured as a cup substantially as described in U.S. Pat. No. 4,024,857, referred to above. As will be appreciated, further, by practitioners-in-the-art, the top may be configured differently as well so long as the scoop arrangement is configured as shown to extend outwardly and inwardly of the cap with the large engaging tip or outer end 24 for engaging a puncture wound and transferring rapidly blood from the engaging tip to the internal surface of container 44. Moreover, the cap includes a vent 30 for air displacement, as will be appreciated, for the rapid introduction of the collected blood into the container 44. As shown in FIG. 4, vane 28 extends from a point 42 outwardly of the end wall of top surface 18 of cap 10, and inwardly to ribs 82, 84 to be described below.

Figure 3:
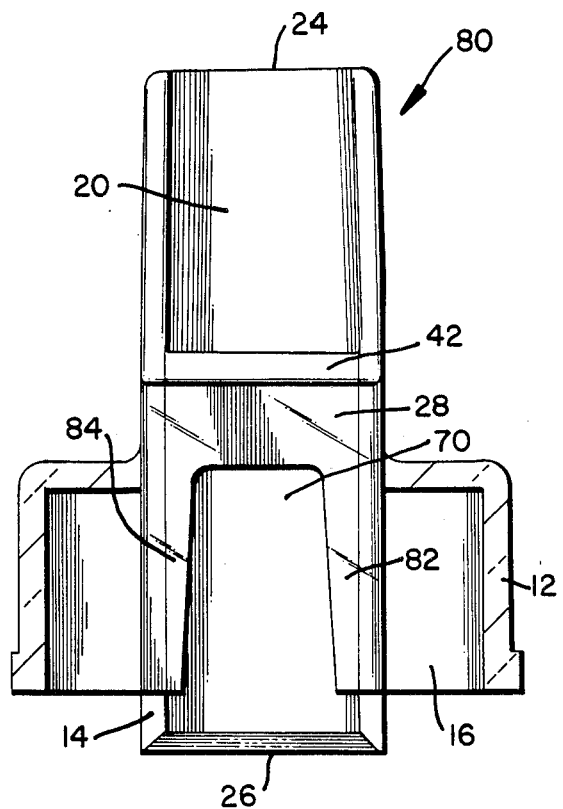
FIG. 3 is a view of the collector of FIG. 1 as viewed from the right-hand side thereof.
Figure 6:
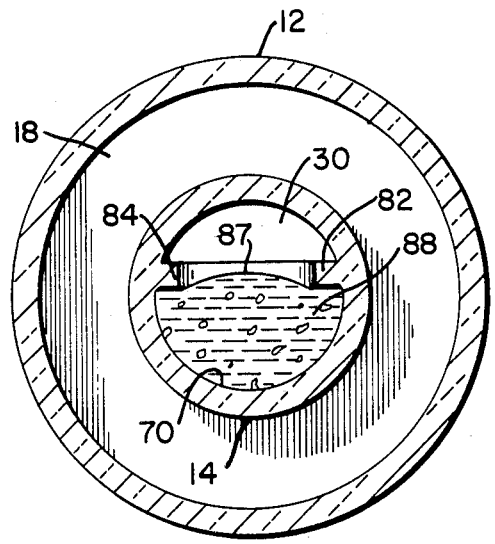
FIGS. 6 and 7 are sectional views taken along line 6, 7—6, 7 of FIG. 1, and illustrating two forms of blood flow through the collector passage of the invention.
Figure 7:
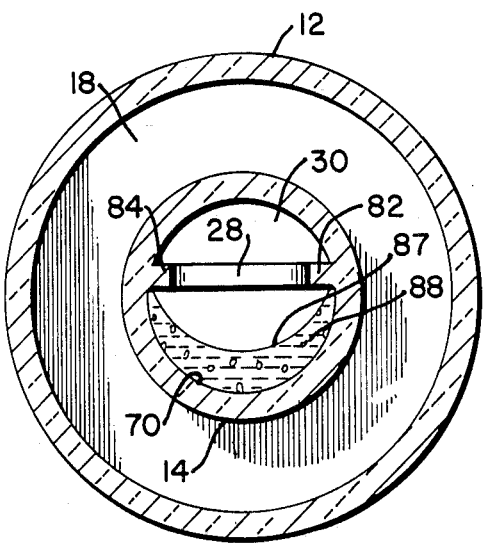

Referring now to FIGS. 3, 6 and 7 in accordance with this invention, vane 28 ends at point 81 in a pair of opposed ribs 82, 84. For this reason passages 30 and 70 are open to each other rearwardly from point 81 toward the rear end edge 26 of collector 10. For this reason, blood 88, as shown in FIGS. 6 and 7 for illustration purposes, does not come into contact with walls over the entire circumferential extent of passage 70. For this reason there is no capillary action causing blood "hang-up" in passage 70 since top surface 87 of the blood 88 is exposed to air passage 30.

Figure 8:
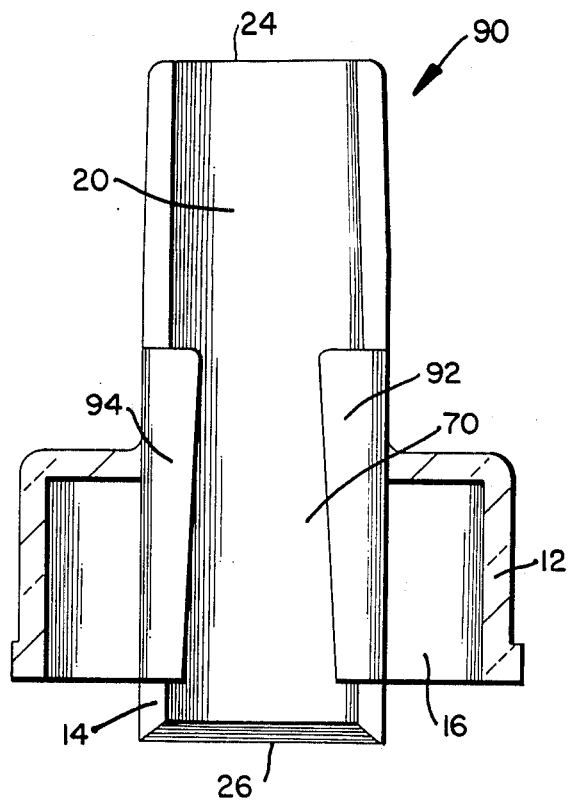
FIG. 8 is a view similar to that of FIG. 3, but illustrating a modified form of collector of the invention.

FIG. 8 illustrates a modified form of collector of the invention. In this embodiment, there is no vane 28 at all adjacent the rear end of the scoop 20. Thus, opposed ribs 92, 94 extend throughout the length of the combined blood passage 70, air passage 30.

One of the aspects of the use of the longitudinally extending opposed ribs 82, 84 or 92, 94 of the invention is the fact that the presence of the ribs has the effect of "containing" the blood flow in passage 70 so that the blood does not build up to the extent of filling passage 30. For this reason, with the arrangement herein, capillary action causing blood "hang-up" is avoided in the collector. As a result there is rapid transfer of blood from the incision to the blood collector.

Figure 5:
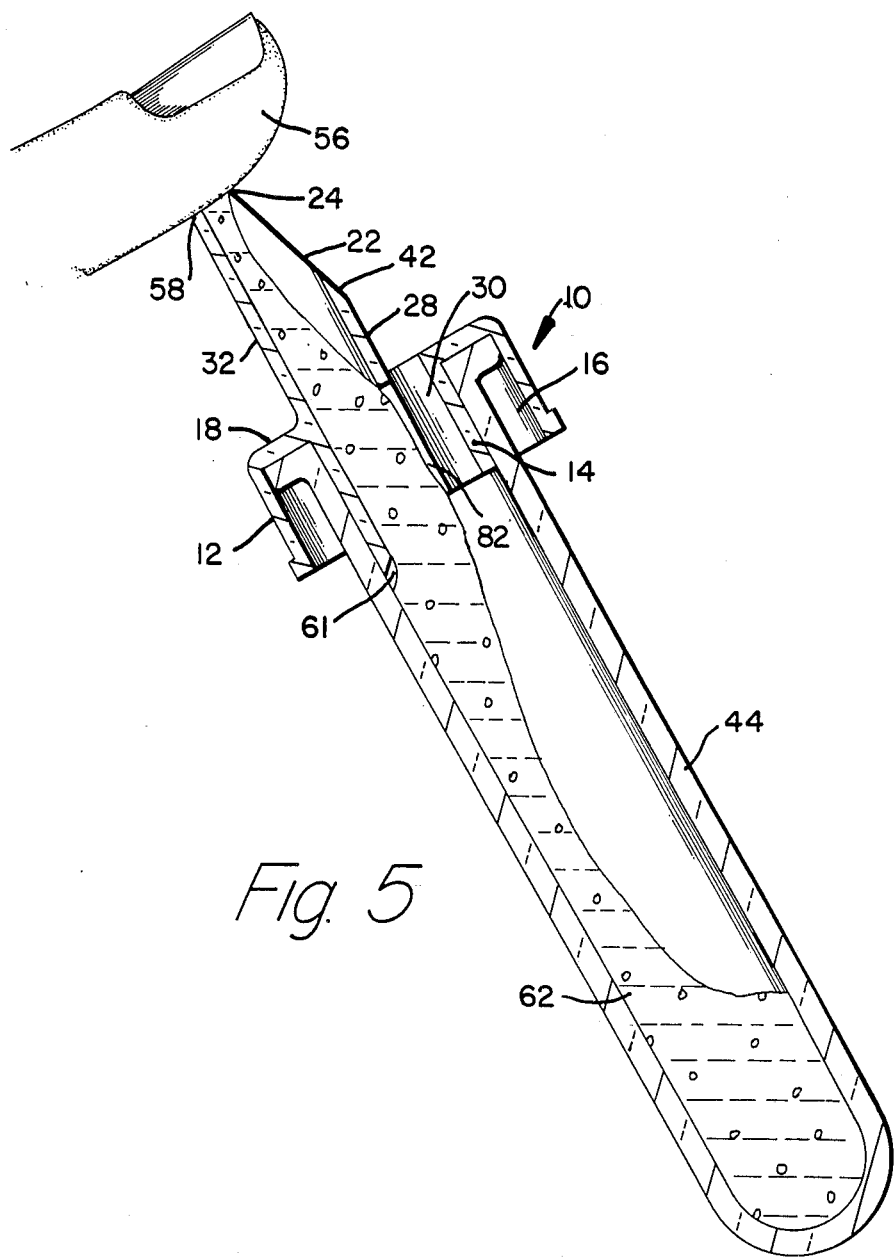
FIG. 5 is a view similar to that of FIG. 4 showing a microcollector device of the invention illustrating the receipt thereof of a quantity of blood from a puncture wound.

In FIG. 5, the arrangement of the invention is shown. The outer engaging tip 24 of the blood collection scoop of the invention, in accordance herewith, has an engaging tip extending over a large angular extent. Therefore, the relative angular positioning of the collection container 44 need not be nearly so precise in order to provide a proper engagement of the tip 24 for a rapid collection and transfer of blood into the container 44. In addition, the transfer area 61 provides a large angular extent for engaging the internal surface of the microcollection container 44 for preserving the rapid flow of blood into and along the internal surface of container 44. As will be appreciated by practitioners-in-the-art, it is most important for these small quantities of collected blood to be transferred rapidly into the collection container. Otherwise, the blood will clot. With the improved collector of the invention, the flow of collected blood from tip 24 to area 62 is much more rapid, and an immediate transfer of the specimen from tip 24 to area 62 is achieved.

For example, with the form of collector taught in U.S. Pat. No. 4,397,318, it takes, on average, about six drops of blood from a wound to initiate flow through the collector. By contrast, only about two drops are required, on average, for the collector of the invention here, a 300 percent plus improvement in speed of collection. Moreover, one of the problems with the very small microcollection devices of the kind discussed here is the formation of air pockets in the bottom of the container. The formation occurs always with previous collectors but only ten percent in the device of the invention, a vast improvement. Of course, reducing the need for surfactants reduces their associated cost making the device of the invention much more attractive for those who must purchase and use such devices on a continuous basis.

While the microcollection scoop of the invention may be separately configured to be inserted into a cap for a microcollection container with the scoop incorporating its own defined blood air vent passages, preferably, the microcollection scoop will be incorporated into an integral structure with the cap or top of the microcollection container involved. Preferably, it will be of a clear molded thermoplastic such as polyethylene, for example. Other materials which may be used, as will be appreciated by practitioners-in-the-art, include various thermoplastics such as polypropylene and polyvinyl chloride.

Whereas, as discussed above, specific embodiments of microcollection containers and associated tops or caps have been shown, it should be understood that it is within the purview of this invention to provide other forms of microcollection containers with differently configured cooperating caps or tops, as long as they can be configured to receive the introduction of the microcollection scoop arrangement of the invention here utilizing an air displacement vent area protected by properly extending separate segregation ribs.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. A blood collector for a microcollection container, comprising
   (a) a collector body having a blood flow passage therethrough;
   (b) said body extending from a puncture wound engaging front end surface to a blood discharge rear end surface;
   (c) means on said body for attaching said body to a microcollection container;
   (d) vent means in said body for air displacement therethrough;
   (e) said puncture wound engaging front end surface being the front end of said blood flow passage and having a large circumferential extent;
   (f) said blood flow passage and said vent means forming a single passage through said collector body;
   (g) a pair of longitudinal ribs extending along the length of said single passage from a first front end intermediate said single passage to a second rear end adjacent said blood discharge rear end surface;
   (h) one each of said pair of ribs positioned on opposite side of said single passage at points radially spaced from each other; and
   (i) said ribs dividing said single passage into said blood flow passage and said vent means.

2. The apparatus of claim 1, further characterized by
   (a) a vane partially dividing said single passage into said blood flow passage and said vent means;
   (b) said vane extending from said first front end of said ribs to a point spaced from said puncture wound engaging front end surface; and
   (c) the upper edge of said body being tapered from said puncture wound engaging front end surface to the front edge of said vane to form blood flow passage scoop means.

3. The apparatus of claim 1, further characterized by
   (a) said collector body being semi-tubular and the walls thereof extending circumferentially through an angle of about 120° at said front end surface.

4. The apparatus of claim 1, further characterized by
   (a) said rear end surface extends rearwardly to a point spaced from said attaching means.

5. The apparatus of claim 1, further characterized by
   (a) said rear end surface having a large circumferential extent.

6. The apparatus of claim 5, further characterized by
   (a) the walls of said collector body extending circumferentially through an angle of about 220° at said rear end surface.

7. The apparatus of claim 1, further characterized by
   (a) said attaching means comprises
      (1) inner and outer concentric annular skirts spaced from each other to define container end wall engaging surfaces;
      (2) a top wall joining one end of said concentric skirts; and
   (b) said collector body extending through said skirts.

8. The apparatus of claim 7, further characterized by
   (a) said collector body and said vent means being positioned adjacent to each other in said attaching means separated by said pair of ribs;
   (b) said adjacent collector body and said vent means together being annular in cross section; and
   (c) a portion of the longitudinal extent of said annular adjacent collector body and vent means forming said inner skirt.

9. A blood collector closure for a microcollection container, comprising
   (a) a cap for engaging the open end of a microcollection container;
   (b) a longitudinally extending collector body extending through said cap and having a blood flow passage therethrough;
   (c) said collector body extending beyond said cap at each end thereof from a puncture wound engaging front end surface to a blood discharge rear end surface;
   (d) vent means in said cap for air displacement therethrough;
   (e) said puncture wound engaging front end surface being the front end of said blood flow passage and having a large circumferential extent,
   the improvement characterized by
   (f) said blood flow passage and said vent means forming a single passage through said collector body;
   (g) a pair of longitudinal ribs extending along the length of said single passage;
   (h) one each of said pair of ribs positioned on opposite sides of said single passage at points radially spaced from each other; and
   (i) said ribs dividing said single passage into said blood flow passage and said vent means.

10. The apparatus of claim 9, further characterized by
    (a) said collector body having walls being semi-tubular and extending circumferentially through an angle of about 120° at said front end surface.

11. The apparatus of claim 10, further characterized by
    (a) said rear end surface having a large circumferential extent.

12. The apparatus of claim 11, further characterized by
    (a) the walls of said semi-tubular collector body extending circumferentially through an angle of about 220° at said rear end surface.

13. The apparatus of claim 9, further characterized by
    (a) said cap comprises
       (1) inner and outer concentric annular skirts spaced from each other to define a container end wall engaging surface; and
       (2) a top wall joining one end of said concentric skirts.

14. The apparatus of claim 13, further characterized by
    (a) said collector body and said vent means being positioned adjacent to each other in said single passage separated by said pair of ribs;
    (b) said adjacent collector body and said vent means together being annular in cross section;
    (c) a portion of the longitudinal extent of said annular adjacent collector body and vent means forming said inner skirt.

* * * * *